US00PP12459P2

(12) United States Plant Patent

Bak et al.

(10) Patent No.: US PP12,459 P2
(45) Date of Patent: Mar. 12, 2002

(54) GUZMANIA PLANT NAMED 'SOLEDO'

(75) Inventors: Elly Bak, Rijsenhout; Nicolaas D. M. Steur, Oude Niedorp, both of (NL)

(73) Assignee: Corn. BaK B.V., Assendelft (NL)

( * ) Notice: Subject to any disclaimer, the term of this patent is extended or adjusted under 35 U.S.C. 154(b) by 0 days.

(21) Appl. No.: 09/521,883

(22) Filed: Mar. 9, 2000

(51) Int. Cl.[7] ..... A01H 5/00

(52) U.S. Cl. ..... Plt./371

(58) Field of Search ..... Plt./371

(56) References Cited

PUBLICATIONS

GTITM UPOVROM Citation for 'Soledo' as per QZ PBR 991138; Aug. 9, 1999.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Soledo' particularly characterized by its solid growth habit in a funnel-form rosette measuring approximately 32 cm in height above the pot when flowering. The leaves are numerous and relatively narrow, each approximately 5.0–5.5 cm in width and 34 cm in length. 'Soledo' has a superior floral bract production, compound inflorescence, long-lasting habit, and yellow-red floral bracts, which especially distinguishes the new cultivar from others, including the cultivar 'Red Star'.

1 Drawing Sheet

BACKGROUND OF THE INVENTION

The present invention comprises a new and distinct cultivar of Guzmania that is an inter-specific hybrid, hereinafter referred to by the cultivar name 'Soledo'.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

Methods for cultivation and crossing of Guzmania are well known. For a detailed discussion, reference is made to the following publications, which are incorporated herein by reference: Benzing, David H., *THE BIOLOGY OF THE BROMELIADS*, Mad River Press, Inc., Eureka (1980); Zimmer, Karl, *BROMELIEN*, Verlag Paul Parey, Berlin (1986); and Rauh, Werner, *BROMELIEN*, Verlag Eugen Ulmer, Stuttgart (1981).

The new cultivar 'Soledo' is a product of a planned breeding program and was originated by the inventors from a cross made during such a program in Assendelft, The Netherlands, in 1989. The male or pollen parent was a proprietary selection of *Guzmania lingulata* identified by Code No. 8940920. The female or seed parent was a proprietary selection of *Guzmania squarrosa* identified by Code No. 8940906.

The selection which is the variety 'Soledo' was chosen after commencement of flowering of the progeny of the cross of 8940920×8940906 in 1992 in Assendelft, The Netherlands. The selection was first asexually propagated through offshoots by, or under the supervision of, the inventors in Assendelft, The Netherlands, with subsequent asexual reproduction through the use of tissue culture. Continuous asexual propagation has demonstrated that the combination of characteristics as herein disclosed for the new cultivar 'Soledo', as observed in Assendelft, The Netherlands, are firmly fixed and reproduce true to type through successive generations of asexual reproduction.

'Soledo' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar. For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The closest comparison cultivar is Guzmania 'Red Star' (U.S. Plant Pat. No. 8,613). The most important difference is the color of the inflorescence. The inflorescence of Guzmania 'Soledo' is yellow, RHS 12A and green, RHS 143B in color. Guzmania 'Red Star' has bright red scape bracts, RHS 42A through 45A and 45C, and flower petals when visible are yellow, RHS 13C. Plants of the new cultivar differ from its parents primarily in plant height.

BRIEF DESCRIPTION OF THE INVENTION

'Soledo' is particularly characterized by the following characteristics:

1. Steady growth habit in a funnel-form rosette measuring approximately 32 cm in height above the pot when flowering;
2. Numerous, relatively narrow leaves, each approximately 5.0–5.5 cm in width and 34 cm in length;
3. Superior primary bract production;
4. Compound inflorescence;
5. Floral bracts are yellow-red, which especially distinguishes the new cultivar from others known to the inventors, including the cultivar 'Red Star'; and
6. Long-lasting leaves and inflorescence color.

Guzmania 'Soledo' is a steady, long-lasting hybrid with superior bract-production and a compound, yellow and green inflorescence that exhibits good keeping quality.

BRIEF DESCRIPTION OF THE DRAWINGS

The accompanying color photographic illustration shows typical inflorescence and foliage characteristics of 'Soledo', with colors being as true as possible with illustrations of this type.

DETAILED BOTANICAL DESCRIPTION

The following traits have been repeatedly observed and in combination distinguish 'Soledo' as a new and distinct cultivar. These observations, measurements and descriptions were taken of 13 to 15 month old 'Soledo' plants grown under greenhouse conditions which approximate those generally used in commercial practice. In the following description, color references are made to The Royal Horticultural Society (R.H.S.) Colour Chart. The new cultivar flowers approximately 18 weeks after treatment with acetylene.

Plant:

*Form*.—Funnel-form rosette.
*Height*.—Approximately 32 cm high, when flowering.
*Growth habit*.—Stemless.
*Diameter*.—Approximately 54 cm.
*Crop time*.—It takes approximately 13 to 15 months after potting to have a fully grown, mature plant.

Foliage:

*Color*.—Upper surface: RHS 147A. Under surface: RHS 147A with RHS 187A.
*Size of leaf*.—Length: Approximately 34 cm. Width: Approximately 5.0–5.5 cm.
*Shape of leaf*.—Linear-lanceolate.
*Surface texture*.—Smooth.
*Leaf shape*.—Broad linear.
*Apex*.—Acute.
*Margin*.—Entire.
*Orientation*.—Leaf blades arch continuously from the base.
*Variegation*.—None.
*Number of leaves*.—Approximately 25.

Bracts:

*Scape bracts*.—Length: The lowest are approximately 32 cm long. The scape bracts just below the primary bracts are approximately 9 cm long. Width: Approximately 4.5–5.5 cm. Number: Approximately 10. General Shape: Lanceolate. Texture: Smooth. Apex: Acute. Margin: Entire. Color: RHS 161C (both surfaces).
*Primary bracts*.—Length: The lowest are approximately 9 cm long. The bracts progress upwardly, they become shorter, with the top primary bracts being approximately 4 cm in length. Width: Approximately 3.0–5.0 cm. Number: Approximately 10. General shape: Lanceolate. Texture: Smooth. Apex: Acute. Margin: Entire. Color: Red RHS 53B and yellow RHS 12B (both surfaces); red apices 53B, green apices RHS 161C.
*Top primary bracts*.—Apex: Acute. Color: RHS 12A (both surfaces).

Flowers:

*Borne (stalks)*.—Erect.
*Type of inflorescence*.—Compound.
*Form*.—Panicle.
*Size of inflorescence on stalk*.—Approximately 12 cm high and approximately 15 cm in diameter.
*Individual petals*.—(Mostly disposed within the floral bracts hidden behind the primary bracts). Length: Approximately 4.0–4.5 cm. Width: Approximately 0.5 cm. Quantity: Approximately 60 flowers divided over approximately 10 branches depending on the size of the plant. Color: Yellow, RHS 17A (both surfaces).
*Time of blooming*.—A fully grown plant can bloom throughtout the entire year starting approximately eighteen (18) weeks after natural induction or through treatment with acetylene.
*Duration of blooms*.—Each flower blooms one (1) day; with several flowers blooming, the total of blooming time for the plant is approximately five (5) weeks.

Reproductive organs:

*Ovaries*.—Superior.
*Stamens*.—Six (6) in number.

Seed characteristics: Sterile hybrid, therefore, no seed or fruit produced.

Pest/disease resistance/susceptibility: No observations made to date.

We claim:

1. A new and distinct cultivar of Guzmania plant named 'Soledo', substantially as illustrated and described.

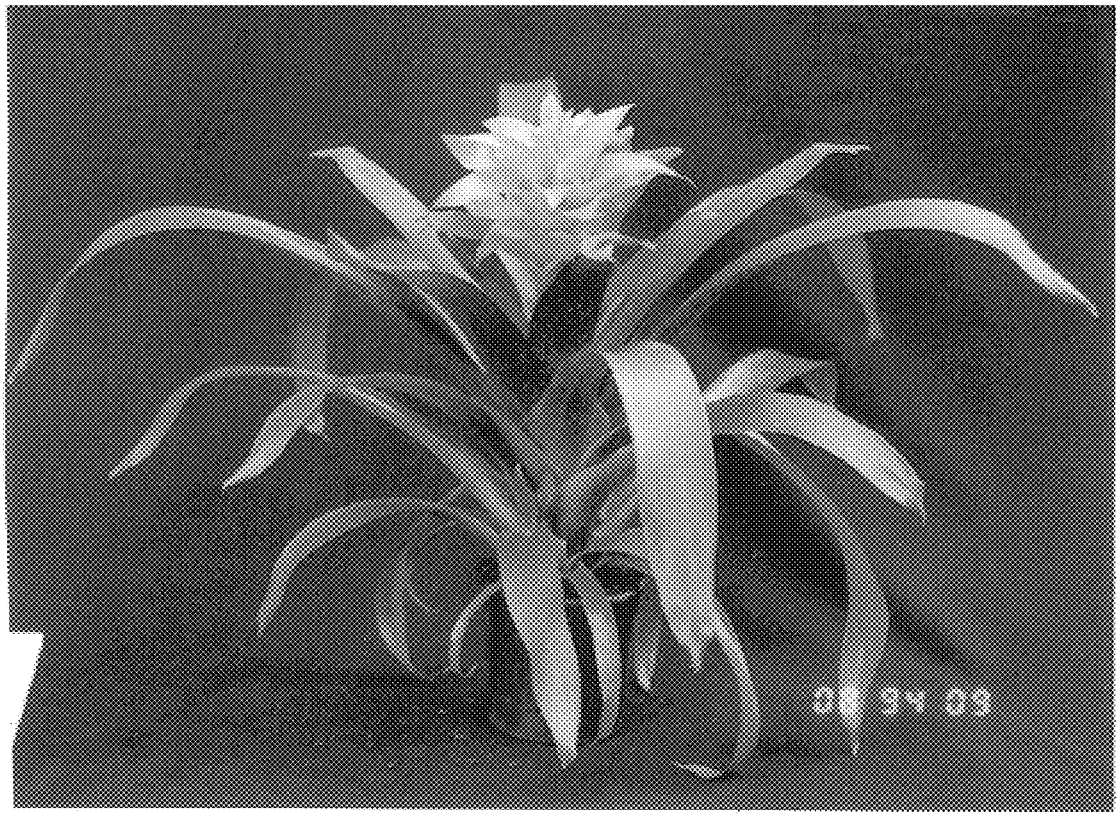

* * * * *